United States Patent [19]

Misaki et al.

[11] 4,427,771

[45] Jan. 24, 1984

[54] ASSAY METHOD FOR AMYLASE ACTIVITY AND METHOD OF PRODUCING MALTOSE DEHYDROGENASE FOR USE THEREIN

[75] Inventors: Hideo Misaki; Eiji Muramatsu; Hidehiko Ishikawa; Kazuo Matsuura, all of Shizuoka, Japan

[73] Assignee: Toyo Jozo Kabushiki Kaisha, Tagata, Japan

[21] Appl. No.: 311,263

[22] Filed: Oct. 14, 1981

[30] Foreign Application Priority Data

Oct. 14, 1980 [JP] Japan ................................. 55-144063

[51] Int. Cl.$^3$ .......................... C12N 1/20; C12Q 1/40; C12Q 1/32; C12R 1/11
[52] U.S. Cl. ..................................... 435/22; 435/26; 435/253; 435/837
[58] Field of Search ..................... 435/22, 26, 190, 15, 435/14, 253, 837, 18

[56] References Cited

U.S. PATENT DOCUMENTS

| | | | |
|---|---|---|---|
| 3,869,348 | 3/1975 | Gindler | 435/22 |
| 4,036,697 | 7/1977 | Pierre et al. | |
| 4,097,336 | 6/1978 | Pierre et al. | |
| 4,242,446 | 12/1980 | Madappally et al. | 435/22 |
| 4,271,265 | 6/1981 | Deneke et al. | 435/26 |

FOREIGN PATENT DOCUMENTS

| | | | |
|---|---|---|---|
| 54-118297 | 9/1979 | Japan | 435/22 |
| 55-34007 | 3/1980 | Japan | 435/22 |
| 55-114287 | 9/1980 | Japan | 435/190 |

OTHER PUBLICATIONS

Rick et al., Methods of Enzymatic Analysis, vol. 2, Academic Press, Inc., New York, 885–890 (1974).
Kobayashi et al., Agr. Biol. Chem., 44(1), 41–47 (Jan. 1980).
Bergmeyer, *Methods of Enzymatic Analysis*, vol. 2, Academic Press, Inc., New York, 890–898 (1974).

Primary Examiner—Esther M. Kepplinger
Attorney, Agent, or Firm—Young & Thompson

[57] ABSTRACT

An assay method for amylase activity in a biological specimen such as serum, saliva or urine. The enzyme amylase in the specimen is used to decompose a substrate which is a glucose polymer having a modified reducing terminal glucose residue or a cyclic glucose polymer. A component of the decomposed substrate is measured as an indication of amylase activity in the specimen. The residue may be amylose, amylopectin, starch, starch hydrolyzate, an etherified reducing terminal, an esterified reducing terminal, gluconolactone or a gluconic acid residue or its derivative. Decomposed substrate assay may be effected by contacting the same with maltose dehydrogenase and NAD or NADP, whereupon the assay is performed by measuring the amount of reduced NAD or reduced NADP, by reacting the same with reduced-form hydrogen transport colorimetric reaction reagent. This reagent may be a tetrazolium salt and diaphorase, or tetrazolium salt and phenazinemethosulfate. To remove pre-existing glucose and maltose present in the specimen, the specimen may be pretreated with alpha-glucosidase or kinase in the presence of $Mg^{++}$ and ATP, the kinase being for example hexokinase. The preferred maltose dehydrogenase is produced by culturing *Bacillus megaterium* B-0779 FERM-P No. 5662.

8 Claims, 8 Drawing Figures

ASSAY METHOD FOR AMYLASE ACTIVITY AND METHOD OF PRODUCING MALTOSE DEHYDROGENASE FOR USE THEREIN

This invention relates to a novel assay method for amylase activity. More particularly, the invention is concerned with an assay method for amylase activity in a sample such as serum, saliva or urine, which comprises assaying the decomposed substrate by enzyme amylase using a glucose polymer having a modified reducing terminal glucose residue or a cyclic glucose polymer as a substrate.

Hitherto known assay methods of amylase activity are based on the fact that a substrate glucose polymer such as starch is hydrolyzed by amylase action to form glucose, maltose or oligo saccharides. Examples are assay methods comprising measurement of the decrease of viscosity of starch by amylase action; iodometry; the reaction of glucose with glucose oxidase or glucose dehydrogenase and NAD (NADP), wherein glucose is formed by the action of α-glucosidase on maltose which is produced from amylase action on starch; and the blue starch method or maltose phosphorylase method comprising colorimetrically measuring the soluble pigment produced by amylase action on insoluble pigment-bound starch (Japan. Pat. Publ. No. 55-27800).

These prior methods have a number of disadvantages, for example: variability of hydrolysis caused by the reagent used and the reaction conditions imposed, and the inhibitory action of coexisting glucose and maltose. Furthermore, in the blue starch method, a complicated separation procedure by centrifugation in required, which impedges automation, and in the maltose phosphorylase method, the four steps of enzyme treatment which are required and which render the operations expensive and difficult.

We have found that amylase activity can be assayed with simplicity and good accuracy, if the reducing terminal group of a glucose polymer having a reducing terminal glucose residue is esterified, etherified or oxidized to form a modified reducing terminal group which cannot be a substrate for maltose dehydrogenase. The glucose polymer having a modified reducing terminal glucose residue thus produced, is then subjected to a substrate for amylase activity assay.

Further advantages are obtainable if the decomposed substrate produced in the enzymatic reaction is dehydrogenated by maltose dehydrogenase with NAD or NADP, and the thus-produced reduced NAD or reduced NADP is directly measured or indirectly measured by a hydrogen transport coloring reagent in reduced form.

Further advantages have been achieved when the samples for amylase assay such as serum, saliva or urine are previously treated with α-glycosidase or kinase such as hexokinase in the presence of $Mg^{++}$ and ATP.

It is accordingly an object of the present invention to provide an amylase assay method which is simple, accurate and well adapted for automation.

Other objects, features and advantages of the present invention will become apparent from a consideration of the following description, taken in connection with the accompanying drawings, in which.

Figure 1:
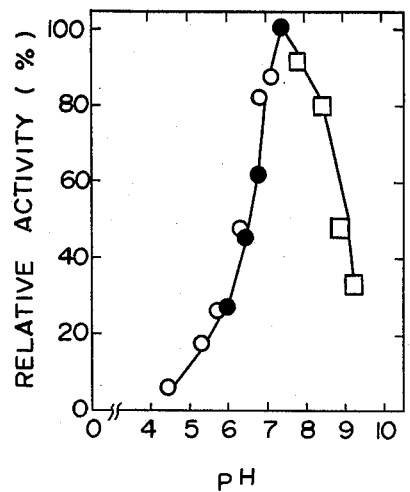
FIG. 1 is a graph of optimum pH, using the enzyme of Example 12.

Examples of substrates useful in the present invention are glucose polymers having modified reducing terminal glucose residues, preferably of a polymerization degree above 5.

Examples of glucose polymers having modified reducing terminal glucose residues are amylose, amylopectin, starch or starch hydrolyzates such as soluble starch (so-called dextrin) in which the reducing terminal glucose residue of the glucose polymer is modified.

The modified reducing terminal glucose residue of the present invention is a residue possessing no reducing activity. Examples are etherified or esterified reducing terminal groups produced by conventional methods or gluconic acid residues of oxidized glucose residue or their esterified derivatives.

Examples of these modifications are as follows:

A soluble of polysaccharides such as soluble starch is reacted with 4% methanolic hydrochloric acid at 70° C. for 4 hours, neutralized, and a fraction collected having a molecular weight above 1000 by gel-filtration column chromatography to obtain methyl-etherified soluble starch. The soluble starch is added to acetic anhydride (3.5 ml) in dry pyridine and reacted at 0° C. overnight. It is then precipitated by adding acetone, and a fraction collected having a molecular weight above 1000 by gel-filtration column chromatography to obtain an acetylated soluble starch.

Soluble starch in Fehling's reagent is boiled for 5 minutes to 20 hours, concentrated, the insolubles removed after addition of methanol and the fraction collected having a molecular weight above 1000 to obtain a compound in which the reducing terminal glucose residues are oxidized to gluconic acid residues which may be optionally esterified.

These modifications of glucose residues are not limited to the above, but can be carried out by other conventional methods. For example, methyl etherification can be replaced by ethyl etherification or isopropyl etherification; or acetylation can be replaced by propionylation; or gluconic acid residues can be replaced by anhydrides such as those of the gluconolactone type. However, the gluconolactone type is usually unstable; and therefore, gluconic acid residues are preferable. The degree of polymerization of glucose need not be limited to a uniform polymerization degree but may include various degrees of polymerization. Examples of cyclic glucose polymers are dextrins with more than six glucose units obtained from starches such as α-, β-, γ-, δ or ξ-cyclodextrin. These substrates are hydrolyzed by amylase in a sample at 37° C. buffered to pH 6-8 to form decomposed substrates such as glucose, maltose and other oligosaccharides. Amylase activity in the sample is assayed by measuring the thus-formed decomposed substrates, and the assay is preferably carried out by a procedure using maltose dehydrogenase and NAD or NADP at 37° C. at pH 6-8.

A preferred example is maltose dehydrogenase produced by culturing *Bacillus megaterium* B-0779 FERM-P No. 5662 (see the Japanese Patent application filed August 29, 1980, entitled "A process for manufacturing maltose dehydrogenase").

The strain *Bacillus megaterium* B-0779 has been isolated from a soil sample from a watermelon field in Ukihashi, Ohito-cho, Tagata-gun, Shizuoka-ken, Japan and has the following taxonomical properties:

A. Growth characteristics:

1. Nutrient agar slant medium:

Good growth, straight, opaque with dull, grayish white to gray. No soluble pigment formation.

2. Nutrient agar plate medium:

Colonies; round, edges wrinkled and surface undulate.

3. Peptone liquid medium:

Weak growth, uniformly turbid, later flocculent precipitation.

B. Morphological characteristics:

Single, double or short twisted chains. Straight large rod, round edges, $1.0-1.5 \times 2.0-3.0\mu$, seldom $1.0-1.5 \times 7.0\mu$. Capsule formed. No motility. Spores difficult to identify with center or nearby edges in cells.

C. Biochemical and physiological properties:

| | |
|---|---|
| Gram stain | + |
| Acid-fast stain | − |
| OF test | O (oxidative) |
| anaerobic growth | − |
| gelatin liquefaction | + |
| starch hydrolysis | − |
| casein hydrolysis | (+) |
| esculin hydrolysis | − |
| catalase | + |
| oxidase | (+) |
| lecithinase | − |
| urease | − |
| SSR medium | − |
| Christenssen medium | − |
| H$_2$S formation | − |
| VP, MR-test | − |
| phosphatase formation | − |
| lysozyme resistance | − |
| indole formation | − |
| nitrate reduction | + |
| citrate utilization (Simons medium) | + |

Acid formation from carbohydrates (no gas formation):

Acid formation: L(+) arabinose, cellobiose, fructose, glucose, glycerol, inulin, maltose, raffinose, sucrose, trehalose, xylose;

No acid formation: adonitol, dulcitol, meso-erythritol, fucose, galactose, inositol, lactose, mannose, melezitose, melibiose, L(+)rhamnose, salicine, L-sorbose, sorbitol, starch.

The G+C content of DNA: 40.1%

As hereinabove explained, the strain B-0779 is identified as belonging to the genus Bacillus on the basis of its characteristics as Gram positive, catalase and oxidase positive, sporulating aerobic large bacilli, no acetoin formation, no lysozyme resistance, no lecithinase production, and acid formation from arabinose, mannitol and xylose. [Bergey's Manual of Determinative Bacteriology, 7th Ed. (1957) and 8th Ed. (1974). Manual for the identification of Medicinal Bacteriology (1974) and Agriculture Handbook, p. 427, The genus Bacillus.]

Furthermore, the strain is referred to as *Bacillus megaterium* on the basis of detailed comparison as shown in Table 1, and is designated *Bacilus megaterium* B-0779.

TABLE 1

| | The Strain B-0779 | Bacillus megaterium (Agriculture Handbook, 427 the genus Bacillus) |
|---|---|---|
| Gram stain | + | + |
| Capsule | + | d |
| Size of cells | 1.0–1.5 × 2.0–3.0 | 1.2–1.5 × 2.0–5.0 |
| Anaerobic growth | − | − |
| Lecithinase | − | − |
| Urease | − | − |
| Lysozyme resistant | − | − |
| Acetoin formation | − | − |
| Phosphatase formation | − | − |
| Arabinose (acid) | + | d |
| Mannitol (acid) | + | + |
| Xylose (acid) | + | d |

Maltose dehydrogenase of the present invention can be obtained by culturing the maltose dehydrogenase-producing microorganism of the present invention in a conventional medium for antibiotic or enzyme production. Cultivation can be carried out in solid or liquid medium. Submerged aeration culture is preferable for industrial production. Nutrient sources for the medium are conventional media for microorganism cultivation. Nutrient sources are assimilable nitrogen sources such as corn steep liquor, peptone, casein, soybean powder, yeast extract or meat extracts. Carbon sources are assimilable carbon sources such as molasses, glucose, glycerol, sucrose or dextrin. Inorganic salts such as sodium chloride, potassium chloride, magnesium sulfate, potassium dihydrogen phosphate or potassium hydrogen phosphate may be added. The culturing temperature can be varied depending on the growth of microorganisms and maltose dehydrogenase production, and is preferably 25°–30° C. The culturing time depends on the conditions and is usually 30–72 hours. Culturation should be terminated at the stage of maximum production of the enzyme. Maltose dehydrogenase of the present invention is contained in the cultured cells.

An example of the enzyme extraction is that isolated cultured wet cells are treated with lysozyme in a tris-HCl buffer, with sonication or the French-press treatment to obtain a crude maltose dehydrogenase solution. The crude enzyme solution is treated by known enzyme isolation and purification procedures to obtain the purified enzyme. Organic solvent precipitation such as with acetone, methanol or ethanol, or salting out with ammonium sulfate, sodium chloride or aluminum sulfate can be used. Further purification can be achieved by adsorption chromatography using an ion-exchanger such as diethylaminoethylcellulose, diethylaminoethyl-dextran gel or triethylaminoethyl-dextran gel, or a gel-filtration agent such as dextran gel or polyacrylamide gel, with lyophilization to obtain the purified maltose dehydrogenase powder.

An assay method and the biochemical properties of the thus-obtained maltose dehydrogenase are as follows:

(1) Assay method:

Reaction mixture (1.00 ml) consisting of the following:

| | |
|---|---|
| 0.2 M tris-HCl buffer (pH 7.5) | 0.4 ml |
| 1% bovine serum albumin | 0.1 ml |
| 0.25% nitrotetrazolium blue (NTB) | 0.1 ml |
| 1% Triton X-100 | 0.1 ml |

-continued

| | |
|---|---|
| 10 mM NADP | 0.1 ml |
| 0.05% phenazine methosulfate (PMS) | 0.02 ml |
| 1M maltose | 0.1 ml |
| distilled water | 0.08 ml |
| Total | 1.00 ml | is pre-incubated at 37° C. for 3 minutes. Enzyme solution (0.05 ml) is added to the reaction mixture and incubated at 37° C. for 10 min. The reaction is stopped by adding 0.1 N HCl (2.0 ml) and the amount of NTBH₂ is colorimetrically measured at 550 nm (optical density: As). Water (0.05 ml) is added as a control and the amount measured at 550 nm (Ab).

The enzymatic reaction of the above is shown as follows:

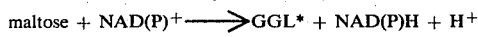

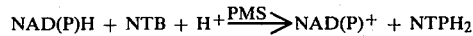

*GGL: O—α-D-glucopyranosyl (1 —→4)-δ-gluconolactone

One unit is defined by the formation 1μ mole of NTBH₂ in one minute and enzyme activity is calculated by the following equation:

$$\text{activity (unit/ml)} = \frac{(As - Ab) \times 3.05}{12.4 \times 10 \times 0.05}$$

$$= (AS - Ab) \times 0.49$$

(2) Substrate specificity:

Maltose in the above assay method is replaced by the substrates in Table 2 (each 0.1 M, 0.1 ml) and assayed according to the above assay method.

TABLE 2

| Substrate | Relative activity (%) |
|---|---|
| maltose | 100 |
| xylose | 0.9 |
| ribose | 2.5 |
| glucose | 15 |
| galactose | 3.9 |
| mannose | 2.8 |
| fructose | 2.9 |
| sucrose | 0 |
| lactose | 98 |
| cellobiose | 44 |
| raffinose | 0 |
| maltotriose | 53 |
| maltopentose | 11 |
| inositol | 0 |
| sorbitol | 0 |
| mannitol | 0 |
| glycerol | 0 |
| 0.5% soluble starch | 0.7 |

As shown in Table 2, maltose dehydrogenase of the present invention has substrate specificity on maltose and lactose.

(3) Coenzymes:

NADP in the assay method hereinabove is replaced by NAD and by a blank (no addition), and activity is measured according to the assay method. The results are shown in Table 3. Maltose dehydrogenase of the present invention requires NADP or NAD as a coenzyme.

TABLE 3

| Coenzyme | Relative activity (%) |
|---|---|
| NADP | 100 |
| NAD | 45 |
| Blank | 0 |

(4) Enzyme action:
The enzyme catalyzes a reaction as follows:

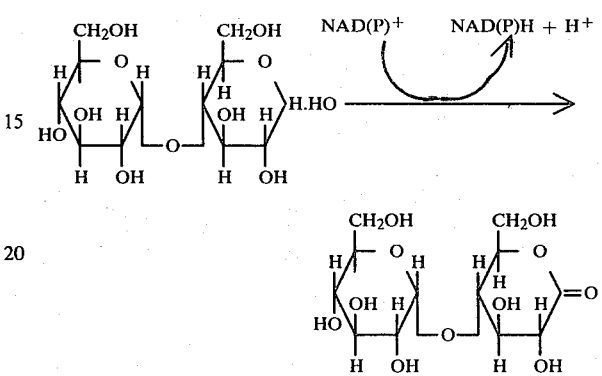

In which GGL and reduced NAD(P) are formed from maltose and coenzyme NAD(P)⁺.

(5) Optimum pH:

| | |
|---|---|
| 1M maltose | 0.1 ml |
| 10 mM NADP | 0.1 ml |
| 0.2 M buffer at various pH | 0.3 ml |
| distilled water | 2.5 ml |
| Total | 3.0 ml |

This reaction mixture is pre-incubated at 37° C. for 3 minutes. Enzyme solution (1 U/ml, 0.03 ml) is added thereto and incubated at 37° C. for 10 minutes. The increase in reduced NADP is measured at 340 nm to determine the optimum pH.

The results are shown in FIG. 1, wherein ○—○: 0.2 M dimethylglutarate-NaOH buffer (pH 4.5–7.2), ●—●: 0.2 M phosphate buffer (pH 6.1–7.4) and □—□: 0.2 M tris-HCl buffer (pH 7.9–9.3).

The optimum pH of maltose dehydrogenase of the present invention is approximately pH 7.5.

Figure 2:
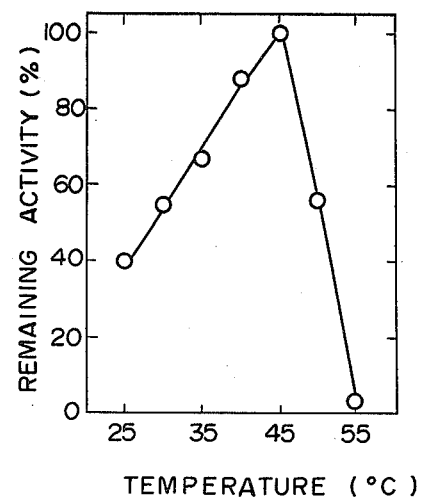
FIG. 2 is a graph of optimum temperature thereof.

(6) Optimum temperature:

Reaction mixture (1.00 ml) as in the (1) assay method hereinabove is heated at various temperatures in the range 25°–55° C. for 3 minutes. Enzyme solution (0.05 U/ml, 0.05 ml) is added thereto, and the mixture is incubated at the temperature in question for 10 minutes. 0.1 N HCl (2.0 ml) is added to stop the enzyme reaction, and then the increased amount of NTBH₂ is measured by optical density at 550 nm. The results are shown in FIG. 2. The optimum temperature of maltose dehydrogenase of the present invention is approximately 45° C.

Figure 3:
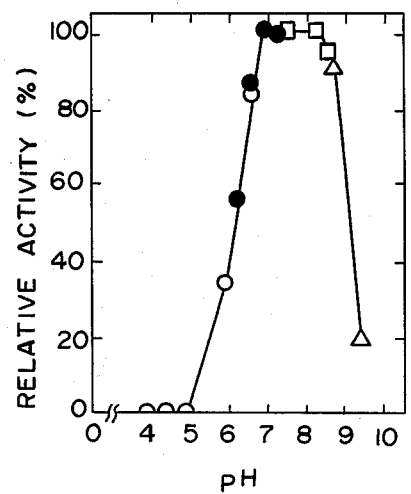
FIG. 3 is a graph of pH stability thereof.

(7) pH stability:

A mixture of enzyme solution (10 U/ml, 0.1 ml), a number of buffer solutions (0.1 ml, each at a different pH) and distilled water (0.8 ml) is pre-incubated at 37° C. for 60 minutes. The reaction mixture is immediately cooled in ice water and enzyme activity is assayed according to the above assay method. The results are shown in FIG. 3. In the figure, ○—○: 0.2 M dimethylglutarate-NaOH buffer (pH 4–6.6), ●—●: 0.2 M phosphate buffer (pH 6.3–7.4), □—□: 0.2 M tris-HCl buffer (pH 7.6–8.6), and △—△: 0.2 M glycine-NaOH buffer (pH 8.7–9.5). The optimum pH stability of maltose dehydrogenase of the present invention is at pH 7–8.5 at 37° C. for 60 minutes treatment.

Figure 4:
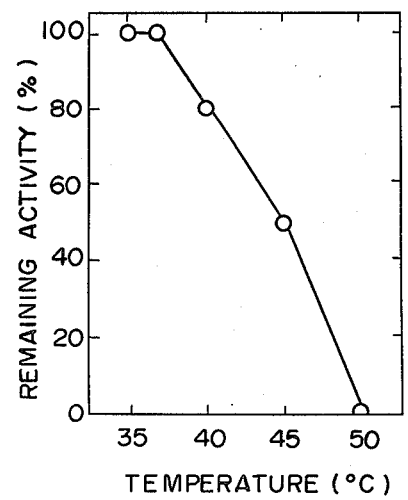
FIG. 4 is a graph of temperature stability thereof.

(8) Heat stability:

A mixture of enzyme solution (10 U/ml, 0.1 ml), 0.2 M Tris-HCL buffer (pH 7.5, 0.1 ml) and distilled water (0.8 ml) is pre-incubated at various temperature in the range 37°–60° C. for 10 min. After treatment, the reaction mixture is cooled in ice water, and then the enzyme activity of the mixture is assayed according to the above assay method. The results are shown in FIG. 4. Maltose dehydrogenase of the present invention has heat stability below 37° C. at pH 7.5 for 10 minutes treatment.

(9) Molecular weight:

Approximately 93,000 (Gel-filtration method using Sephacryl S-200 (trademark)).

(10) Iso-electric point:

Approximately pH 5.1 (electrophoresis using carrier ampholite).

(11) Km value:

Km=3.4×10$^{-2}$M (for maltose)

(12) Effect of metallic ions, PCMB and EDTA:

| | |
|---|---|
| 0.2 M tris-HCl buffer (pH 7.5) | 0.4 ml |
| 0.5% NTB | 0.05 ml |
| 2% Triton X-100 | 0.05 ml |
| 1 M maltose | 0.1 ml |
| 10 mM NADP | 0.1 ml |
| 0.05% PMS | 0.02 ml |
| metallic ion, PCMB or EDTA solution | 0.1 ml |
| distilled water | 0.18 ml |
| Total | 1.00 ml |

The above reaction mixture is pre-incubated at 37° C. for 3 minutes. The enzyme solution (0.05 U/ml, 0.05 ml) is added thereto and incubated at 37° C. for 10 minutes, then enzymatic reaction is stopped by adding 0.1 N HCl (2.0 ml). The optical density at 550 nm is measured for observing the effect of each metallic ion, PCMB and EDTA. The results are shown in Table 4.

TABLE 4

| metallic ion, EDTA or PCMB | relative activity (%) | metallic ion, EDTA or PCMB | relative activity (%) |
|---|---|---|---|
| (no addition) | 100 | 0.01M CoCl$_2$ | 0 |
| 0.1M KCl | 91 | 0.01M ZnCl$_2$ | 0 |
| 0.1M NaCl | 104 | 0.001M CuCl$_2$ | 0 |
| 0.1M NH$_4$Cl | 35 | 0.01M NaN$_3$ | 100 |
| 0.1M LiCl | 89 | 0.0004M PCMB | 126 |
| 001M CaCl$_2$ | 77 | 0.01M EDTA | 134 |
| 0.01M MgCl$_2$ | 16 | 0.001M EDTA | 114 |
| 001M BaCl$_2$ | 106 | 0.0001M EDTA | 110 |
| 0.01M MnCl$_2$ | 0 | | |

(13) Effect of surface-active agent:

| | |
|---|---|
| 1 M maltose | 0.1 ml |
| 10 mM NADP | 0.1 ml |
| 0.2 M Tris-HCl buffer (pH 7.5) | 0.4 ml |
| surface-active agent | 0.1 ml |
| distilled water | 2.3 ml |
| Total | 3.0 ml |

The above reaction mixture is pre-incubated at 37° C. for 3 minutes. Enzyme solution (1 U/ml, 0.05 ml) is added thereto and incubated at 37° C. for 10 minutes. The increased optical density at 340 nm caused by reduced NADP is measured to determine the effect of the surface-active agent. The results are shown in Table 5.

TABLE 5

| Surface-active agent (%) | Relative activity (%) |
|---|---|
| Control | 100 |
| Triton X-100 (0.1) | 98 |
| Triton X-100 (0.5) | 105 |
| Triton X-100 (1) | 107 |
| Adekatol SO-145 (trademark) (0.1) | 105 |
| Adekatol SO-145 (trademark) (0.5) | 102 |
| Adekatol SO-145 (trademark) (1) | 126 |
| Sodium dodecyl sulfate (0.1) | 6 |
| Sodium dodecyl sulfate (0.5) | 0.5 |
| Sodium dodecyl sulfate (1) | 1 |
| Sodium laurylbenzene sulfate (0.1) | 0.5 |
| Sodium laurylbenzene sulfate (0.5) | 1 |
| Sodium laurylbenzene sulfate (1) | 1 |
| Tween-60 (trademark) (0.1) | 92 |
| Tween-60 (trademark) (0.5) | 99 |
| Tween-80 (0.1) | 98 |
| Tween-80 (0.5) | 100 |
| Cation DT (trademark) (0.1) | 100 |
| Cation DT (trademark) (0.5) | 100 |
| Cetyltrimethylammonium chloride (0.1) | 7 |
| Cetyltrimethylammonium chloride (0.5) | 4 |
| Sodium deoxycholate (0.1) | 116 |
| Sodium deoxycholate (0.5) | 127 |

The above biochemical properties indicates that the enzyme of the present invention has weak substrate specificities on lactose, cellobiose and maltotriose, and strong specific activity on maltose. These substrate specificities and other enzymatic action and other properties indicate that the enzyme is properly referred to prior known maltose dehydrogenase [NAD(P)-Dependent Maltose Dehydrogenase; Agr. Bio. Chem., 44(1), 41–47 (1980)].

Maltose dehydrogenase used in the present invention is not restricted to the above enzyme. For example, maltose dehydrogenase obtained from culturing a strain Corynebacterium sp. No. 93-1 [Agr. Biol. Chem., 44(1), 41–47 (1980)] can also be used.

As explained hereinbefore, the decomposed substrate such as maltose, glucose, or oligosaccharides such as maltotriose and maltopentose can be dehydrogenated to form reduced NAD or NADP.

The thus-formed reduced NAD or reduced NADP can be directly measured by absorption at 340 nm for amylase activity assay, or reduced NAD or reduced NADP is reacted with hydrogen transport color reagent and hydrogen is transferred to the other transport system which is indirectly measured for determining the amylase activity.

Examples of the indirect assay system of hydrogen transport color reagent are, for example, reagents comprising tetrazolium salt and diaphorase, or tetrazolium salt and phenazinemethosulfate.

The resulting reaction product is colorimetrically measured by absorption at 550 nm.

Preferred examples of amylase assay systems are (1) a reaction mixture comprising 0.2 M tris-HCl buffer 0.4 part, 1% bovine serum albumin 0.1 part, 0.25% NTB 0.1 part, 1% Triton X-100 0.1 part, 10 mM NAD(P) 0.1 part, 0.05% PMS 0.02 part, 10% substrate solution 0.1 part, 200 U/ml maltose dehydrogenase 0.05 part and distilled water 0.03 part; or (2) a mixture comprising 0.2 M tris-HCl buffer 0.3 part, 10 mM NAD(P) 0.1 part, 10% substrate solution 0.1 part, 200 U/ml maltose dehydrogenase 0.05 part and distilled water 0.45 part.

Generally, one part of either of these reaction mixtures is mixed with sample (0.01–0.5 part) and incubated at 37° C. for a suitable time such as 5 minutes. After termination of the reaction, the mixture is measured as to optical density, as above.

The samples to be assayed are serum, urine or saliva and are optionally diluted for assay. Sometimes the samples contain glucose or maltose. Maltose can be deleted by decomposing to glucose with α-glucosidase, and the glucose is phosphorylated by kinase such as hexokinase or glucokinase in the presence of ATP, $Mg^{++}$ (preferably $MgCl_2$) to glucose-6-phosphate. Also maltose is phosphorylated by maltose phosphorylase. By these treatments, any glucose or maltose present is transformed to compounds which do not affect soluble oxygen in the sample or amylase activity assay.

As hereinabove explained, the present invention relates to an assay method for amylase activity such as α- or β-amylase in a sample, which comprises decomposing the substrate such as a glucose polymer having a modified reducing terminal glucose residue, by the action of amylase activity in the sample, preferably reacting the said decomposed substrate with maltose dehydrogenase and NAD or NADP, and quantitatively measuring directly or indirectly the resulting reduced NAD or reduced NADP. More preferably the present invention can be performed with the additional treatment in that any glucose or maltose present is converted to glucose-6-phosphate by kinase in the presence of α-glucosidase, $Mg^{++}$ and ATP.

The amylase activity assay method of the present invention is a simple and accurate method which may be performed with a kit comprising the above reagents, and can be used for automatic assay.

The following examples illustrate the present invention but are not to be construed as limiting.

EXAMPLE 1

| | |
|---|---|
| 0.2 M tris-HCl buffer (pH 7.4) | 0.4 ml |
| 1% bovine serum albumin | 0.1 ml |
| 0.25% NTB | 0.1 ml |
| 1% Triton X-100 | 0.1 ml |
| 10 mM NADP | 0.1 ml |
| 0.05% PMS | 0.02 ml |
| 10% oxidized soluble starch* | 0.1 ml |
| 200 U/ml maltose dehydrogenase** | 0.05 ml |
| distilled water | 0.03 ml |
| Total | 1.0 ml |

*glucose polymer having a modified reducing terminal glucose residue (gluconic acid residue) obtained in Example 9 (oxidized starch hydrolyzate).
**produced according to Example 12.

Eight aliquots of the above reaction mixture (1.0 ml each) were pre-incubated at 37° C. for 3 minutes. Saliva (20 μl, 300-fold dilution) was added to each and the mixtures were incubated at 37° C. for 0, 2.5, 5, 10, 15, 20, 25 and 30 minutes, respectively. After each reaction, 0.1 N HCl (2.0ml) was added and the mixture was measured at 550 nm by colorimetry.

Figure 5:
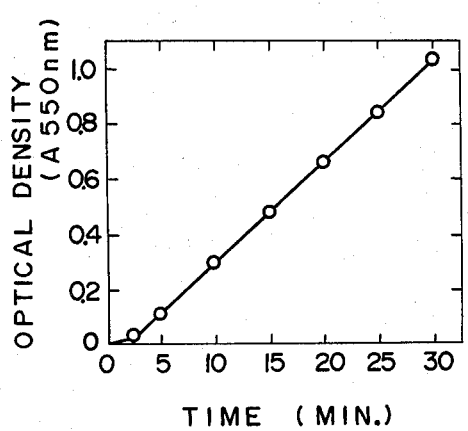
FIGS. 5 and 6 are graphs of amylase activity assay in saliva, as to time and amount.

The results are shown in FIG. 5, wherein good linearity was obtained after 2.5 minutes of initial time lag.

EXAMPLE 2

The same reaction mixture described in Example 1 was pre-incubated at 37° C. for 3 minutes. 1000-fold diluted saliva, in samples of 0, 10, 20, 30, 40 and 50 μl, respectively, were added to each of six 1.0 ml aliquots thereof and incubated at 37° C. for 10 minutes. After incubation, 0.1 N HCl (2.0 ml) was added to each and each medium was colorimetrically assayed at 550 nm.

Figure 6:
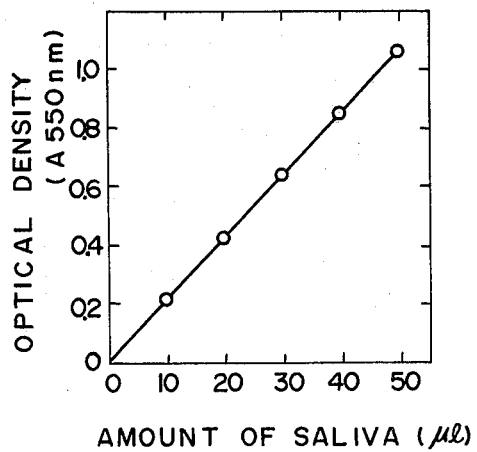

The results are shown in FIG. 6, in which good linearity was obtained.

EXAMPLE 3

| Reaction mixture I: | |
|---|---|
| 0.2 M trist-HCl buffer (pH 7.5) | 0.2 ml |
| 1% bovine serum albumin | 0.1 ml |
| 0.25% NTB | 0.1 ml |
| 1% Triton X-100 | 0.1 ml |
| 10 mM NADP | 0.1 ml |
| α-glucosidase (200 U/ml) | 0.1 ml |
| hexokinase (100 U/ml) | 0.1 ml |
| 100 mM $MgCl_2$ | 0.05 ml |
| 0.05% PMS | 0.02 ml |
| Total | 0.87 ml |
| Reaction mixture II: | |
| 10% oxidized soluble starch* | 0.1 ml |
| 200 U/ml maltose dehydrogenase | 0.05 ml |
| 200 mM EDTA | 0.05 ml |
| Total | 0.2 ml |

*glucose polymer having a modified reducing terminal glucose residue (gluconic acid residue) obtained in Example 9 (oxidized soluble starch).

Reaction mixture I (0.8 ml) was pre-incubated at 37° C. Serum (50 μl) was added thereto and incubated at 37° C. for 5 min. for removing coexisting glucose and maltose. Reaction mixture II (0.2 ml) was added thereto and incubated at 37° C. for 0, 2.5, 5, 10, 15, 20 and 25 minutes, respectively. At the end of each reaction time, 0.1 N HCl (2.0 ml) was added and each medium was colorimetrically measured at 550 nm.

Reaction mixture I′ which contained no hexokinase was used as a control.

Figure 7:
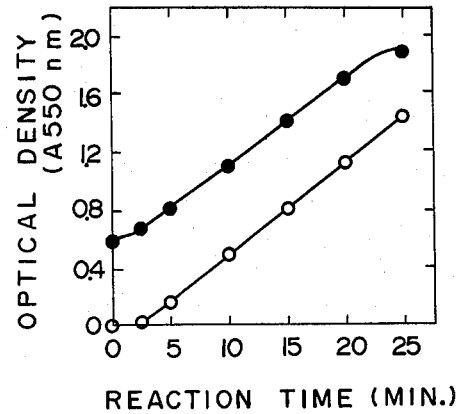
FIGS. 7 and 8 are graphs of amylase activity in serum in terms of reaction time and serum dilution ratio.

The results are shown in FIG. 7, wherein ○—○: reaction mixture I and II, ●—●: reaction mixture I′ and II. As shown in FIG. 7, the assay method using reaction mixtures I and II gave good results.

EXAMPLE 4

| Reaction mixture I: | |
|---|---|
| 0.2 M tris-HCl buffer (pH 7.5) | 1.2 ml |
| 10 mM NADP | 0.3 ml |
| α-glucosidase (200 U/ml) | 0.1 ml |
| hexokinase (10 U/ml) | 0.1 ml |
| 100 mM $MgCl_2$ | 0.15 ml |
| distilled water | 0.55 ml |
| Total | 2.4 ml |
| Reaction mixture II: | |
| 10% oxidized soluble starch* | 0.3 ml |
| 200 U/ml maltose dehydrogenase | 0.05 ml |
| 200 mM EDTA | 0.15 ml |
| Total | 0.5 ml |

*glucose polymer having a modified reducing terminal glucose residue (gluconic acid residue) obtained in Example 9 (oxidized soluble starch).

Reaction mixture I (2.4 ml) was pre-incubated at 37° C. Serum (50 μl, 1/5-5/5 fold dilution) was added thereto and incubated at 37° C. for 5 minutes. Reaction mixture II (0.5 ml) was added thereto and incubated at 37° C. for exactly 20 minutes, and then the medium was measured at 340 nm.

Reaction mixture I′, which did not contain hexokinase, was used as a control.

Figure 8:
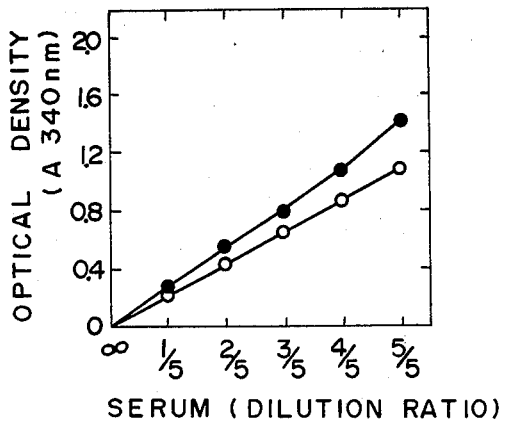

The results are shown in FIG. 8, wherein ○—○: reaction mixture I and II, ●—●: reaction mixture I′ and II. The best results were obtained by assaying using reaction mixtures I and II.

EXAMPLE 5

The substrate in the reaction mixture II in Example 3 was replaced by a 10% solution (0.3 ml) of the glucose polymer having a modified reducing terminal glucose residue (methyletherified glucose residue) obtained in Example 10 to prepare reaction mixture II, and the rest of the procedure was performed as in Example 3.

Results showing good linearity of reaction time and assay were obtained, as shown in FIG. 7.

Optical absorption upon 10 minutes reaction was 0.52.

EXAMPLE 6

The substrate in the reaction mixture II in Example 4 was replaced by a 10% solution (0.3 ml) of the glucose polymer having a modified reducing terminal glucose residue (methyl etherified glucose residue) obtained in Example 10, to prepare reaction mixture II, and the rest of the procedure was performed as in Example 4 using serum of 5/5 fold-dilution. The optical absorption is 1.06, showing good results.

EXAMPLE 7

The substrate in the reaction mixture II in Example 3 was replaced by a 10% solution (0.3 ml) of the glucose polymer having a modified reducing terminal glucose residue (acetylated glucose residue) obtained in Example 11, to prepare reaction mixture II, and the rest of the procedure was performed as in Example 3. Good linearity was obtained for each reaction time, as also is shown in FIG. 7.

EXAMPLE 8

The substrate in the reaction mixture II in Example 3 was replaced by a 5% solution (0.3 ml) of $\gamma$-cyclodextrin to prepare reaction mixture II, and the rest of the procedure was performed as in Example 3. The optical absorption upon 30 minutes reaction was 0.12.

EXAMPLE 9

Soluble starch (50 g) dissolved in water (200 ml) was added to Fehring's reagent (1 lit., containing $CuSO_4.5H_2O$ 35 g, sodium potassium tartrate 173 g and sodium hydroxide 65 g) and boiled for 20 minutes. The reaction mixture was concentrated in vacuo to 300 ml. Methanol (100 ml) was added thereto and the precipitate was removed. The supernatant solution was concentrated to 100 ml and was charged on a column (7×100 cm) of Sephadex G-100 (trademark). Eluate corresponding to a molecular weight above 1000 was collected and lyophilized to obtain a glucose polymer (33.6 g) having a modified reducing terminal glucose residue (gluconic acid residue) (the reducing terminal glucose residue of soluble starch was oxidized as the gluconic acid residue).

EXAMPLE 10

Soluble starch (20 g) suspended in 4% methanolic HCl (400 ml) was reacted at 70° C. for 6 hours. The reaction mixture was neutralized by 5 N NaOH, desalted and concentrated in vacuo. The concentrate was charged on a column (5×100 cm) of Spedhadex G-25 (trademark). Eluate corresponding to a molecular weight above 1000 was collected, concentrated in vacuo and lyophilized to obtain a glucose polymer (8.3 g) having a modified reducing terminal glucose residue of the methylated reducing terminal residue of soluble starch.

EXAMPLE 11

Soluble starch (20 g) in dry pyridine (200 ml) and acetic anhydride (3.5 ml) was reacted at 0° C. overnight. Acetone (1 lit.) was added thereto. The precipitate washed with acetone (200 ml), was dissolved in water and charged on a column (5×100 cm) of Sephadex G-25. Eluate corresponding to a molecular weight above 1000 was collected and lyophilized to obtain a glucose polymer (10.3 g) having a modified reducing terminal glucose residue of the acetylated reducing terminal residue of soluble starch.

EXAMPLE 12

To an aqueous medium (100 ml) comprising dextrin 1%, yeast extract powder 1%, $K_2HPO_4$ 0.1%, KCl 0.05% and $MgSO_4.7H_2O$ 0.05% (sterilized at 120° C. for 20 min., pH 7.2) in a 500 ml Erlenmeyer flask was inoculated one loopful of *Bacillus megaterium* B-0779 FERM-P No. 5662 from bouillon agar slant and shake cultured at 28° C. for 24 hours. The thus-prepared seed culture was transferred into another aqueous medium (20 lit.) comprising dextrin 1%, yeast extract powder 1%, $K_2HPO_4$ 0.1%, KCl 0.05%, $MgSO_4.7H_2O$ 0.05% and silicon SA G-471 (trademark, antifoamer) 0.1% (previously sterilized at 120° C. for 20 min., pH 7.2) in a 300 lit. tank, and submerged cultured at 28° C. for 45 hours, 300 r.p.m., 15 $m^3$/min. aeration. Cultured cells were collected by centrifugation at 5000 r.p.m. for 10 minutes. Wet cells were treated with a solution of 0.1% lysozyme and 5 mM EDTA in tris-HCl buffer (pH 7.5, 4 lit.) at 37° C. for 60 minutes. The solution of solubilized cells was centrifuged (5000 r.p.m., 10 min.) to separate the supernatant (11.8 U/ml, 3.2 lit.). To the supernatant solution was added ammonium sulfate up to 80% saturation and centrifuged (15,000 r.p.m., 10 min.). The precipitate was dissolved in 10 mM tris-HCl buffer (pH 7.5, 200 ml) and centrifuged (15,000 r.p.m., 10 min.). To the supernatant solution (200 ml, 123.5 U/ml) was added 10% calcium chloride (20 ml) and again centrifuged (15,000 r.p.m., 10 min.). Ammonium sulfate was added to the supernatant (200 ml, 85 U/ml) and fractions of 51–63% ammonium sulfate saturation were collected and centrifuged (15,000 r.p.m., 10 min.). The precipitate was dissolved in 10 mM tris-HCL buffer (pH 7.5, 20 ml, 417 U/ml) and charged on a column of Sephadex G-25. The eluate was lyophilized to obtain the purified maltose dehydrogenase (370 mg, 20 U/mg).

From a consideration of the foregoing disclosure, therefore, it will be evident that the initially recited object of the present invention has been achieved.

Although the present invention has been described and illustrated in connection with preferred embodiments, it is to be understood that modifications and variations may be resorted to without departing from the spirit of the invention, as those skilled in this art will readily understand. Such modifications are considered to be within the purview and scope of the present invention as defined by the appended claims.

What is claimed is:

1. An assay method for amylase activity in a biological specimen containing the enzyme amylase, which comprises contacting a said specimen with a substrate which is a glucose polymer selected from the group consisting of amylose, amylopectin, starch and starch hydrolyzate having a lower-alkyl etherified reducing terminal glucose residue, thereby to decompose a portion of said substrate, contacting the decomposed substrate with maltose dehydrogenase and NAD or NADP, and measuring the amount of reduced NAD or NADP as an indication of amylase activity in said specimen.

2. An assay method as claimed in claim 1, wherein the said assay is performed by colorimetric assay comprising a reaction of reduced NAD or reduced NADP with reduced-form hydrogen transport colorimetric reaction reagent.

3. An assay method as claimed in claim 2, wherein the said reduced form hydrogen transport colorimetric reaction reagent is a reagent comprising tetrazolium salt and diaphorase.

4. An assay method as claimed in claim 2, wherein the said reduced form hydrogen transport colorimetric reaction reagent is a reagent comprisng tetrazolium salt and phenazinemethosulfate.

5. An assay method as claimed in claim 1, wherein the said assay is performed by assaying amylase activity in the sample which is pre-treated with α-glucosidase or a kinase in the presence of $Mg^{++}$ and ATP.

6. An assay method as claimed in claim 5, wherein the said kinase is hexokinase.

7. An assay method as claimed in claim 1, wherein the said *Bacillus megaterium* is a strain *Bacillus megaterium* B-0779 FERM-P No. 5662.

8. A method of producing maltose dehydrogenase, comprising culturing *Bacillus megaterium* B-0779 FERM-P No. 5662 in a culture medium, and separating the thus-produced maltose dehydrogenase from the medium.

* * * * *